US009526408B2

(12) United States Patent
Yamaguchi et al.

(10) Patent No.: US 9,526,408 B2
(45) Date of Patent: Dec. 27, 2016

(54) ELECTRONIC ENDOSCOPE SYSTEM AND METHOD FOR CONTROLLING THE SAME

(75) Inventors: Hiroshi Yamaguchi, Kanagawa (JP); Takaaki Saito, Kanagawa (JP); Takayuki Iida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 900 days.

(21) Appl. No.: 13/446,721

(22) Filed: Apr. 13, 2012

(65) Prior Publication Data

US 2012/0265041 A1 Oct. 18, 2012

(30) Foreign Application Priority Data

Apr. 15, 2011 (JP) .................................. 2011-090680
Jan. 13, 2012 (JP) .................................. 2012-004675

(51) Int. Cl.
*A61B 5/1459* (2006.01)
*A61B 1/045* (2006.01)
*A61B 1/06* (2006.01)
*A61B 1/00* (2006.01)

(52) U.S. Cl.
CPC ......... *A61B 1/0638* (2013.01); *A61B 1/00004* (2013.01); *A61B 1/045* (2013.01); *A61B 1/063* (2013.01); *A61B 1/0653* (2013.01)

(58) Field of Classification Search
CPC ..... A61B 1/00004; A61B 1/045; A61B 1/063; A61B 1/0638; A61B 1/0653
USPC .................................. 600/109, 180, 328, 476
See application file for complete search history.

(56) References Cited

U.S. PATENT DOCUMENTS

| | | | | |
|---|---|---|---|---|
| 4,953,539 | A * | 9/1990 | Nakamura et al. | 600/109 |
| 6,416,531 | B2 * | 7/2002 | Chen | A61N 5/0601 |
| | | | | 128/898 |
| 8,585,207 | B1 * | 11/2013 | Bass et al. | 353/31 |
| 2004/0109068 | A1 * | 6/2004 | Mitsunaga et al. | 348/222.1 |
| 2005/0222500 | A1 * | 10/2005 | Itoi | 600/180 |
| 2008/0021331 | A1 * | 1/2008 | Grinvald et al. | 600/476 |
| 2008/0281154 | A1 | 11/2008 | Gono et al. | |
| 2009/0167149 | A1 * | 7/2009 | Ito | 313/501 |
| 2009/0262225 | A1 * | 10/2009 | Yamaguchi et al. | 348/265 |
| 2010/0321772 | A1 * | 12/2010 | Reimer et al. | 359/385 |
| 2012/0057168 | A1 * | 3/2012 | Yuasa | 356/479 |

FOREIGN PATENT DOCUMENTS

JP        6-315477 A   11/1994

\* cited by examiner

*Primary Examiner* — Baisakhi Roy
(74) *Attorney, Agent, or Firm* — Birch, Stewart, Kolasch & Birch, LLP

(57) ABSTRACT

A light source device of an electronic endoscope system has first and second semiconductor lasers. In a vascular observation mode, one of the semiconductor lasers is used in a full light state (100% rated output) while the other is used in a reduced light state (for example, 10% rated output). First and second images of an internal body portion are captured with a color imaging device under illumination of two patterns, respectively. Correlation operation of pixel values of three colors is performed between the two images. Noise components, caused by the first or second semiconductor lasers in the light reduced state, are removed from the first and second images. An oxygen saturation level of blood in a blood vessel is calculated using the first and second images with the noise components removed.

12 Claims, 11 Drawing Sheets

FIRST EMISSION PATTERN

SECOND EMISSION PATTERN

ELECTRONIC ENDOSCOPE SYSTEM AND METHOD FOR CONTROLLING THE SAME

BACKGROUND OF THE INVENTION

1. Field of the Invention

The present invention relates to an electronic endoscope system for imaging an internal body portion using two or more types of illumination light and a method for controlling the same.

2. Description Related to the Prior Art

In the medical field, electronic endoscopes are widely used in medical examinations. The electronic endoscope is provided with an insert section to be inserted into a patient's body. Illumination light is applied to an internal body portion of the patient from a distal end of the insert section. An imaging device disposed in the distal end captures an image of the internal body portion being illuminated.

The electronic endoscope is connected to a lighting device. The illumination light from a light source of the lighting device is supplied to the electronic endoscope. Conventionally, a white light source (e.g. a xenon lamp or a metal halide lamp) has been used. Recently, a technique using narrowband light as the illumination light has attracted attention (see Japanese Patent No. 3583731 corresponding to U.S. Patent Application Publication No. 2008/0281154). The narrowband light is applied to the internal body portion and an image of the reflection light is captured. The use of the narrowband light facilitates finding a lesion.

A method for obtaining vascular information (e.g. an oxygen saturation level of hemoglobin in blood) based on image signals of images has been researched (see Japanese Patent Laid-Open Publication No. 06-315477). In this method, the images are captured under the illumination of the respective different types of narrowband light applied alternately. The method utilizes the narrowband light of wavelength sets in the respective wavelength bands of 300 to 400 nm, around 400 nm, 400 to 500 nm, 500 to 600 nm, and 450 to 850 nm.

A semiconductor light source (e.g. a semiconductor laser diode) has been used for a narrowband light source. Frequent turning on and off of the semiconductor light source causes overshoot of its output mainly due to temperature factors. In other words, a light quantity of the illumination light increases instantaneously after the turning on, making the light quantity unstable and uneven. Thereby, accurate vascular information cannot be obtained. The U.S. Patent Application Publication No. 2008/0281154 and Japanese Patent Laid-Open Publication No. 06-315477 do not disclose solution to the problem.

SUMMARY OF THE INVENTION

An object of the present invention is to provide an electronic endoscope system for preventing unevenness in light quantity due to overshoot of a semiconductor light source and a method for controlling the same.

To achieve the above and other objects, an electronic endoscope system of the present invention includes at least first and second light source system, a color imaging device, a controller, a noise removal section, an image production section, and a display section. The first and second light source systems illuminate an internal body portion including a blood vessel. The first light source system generates first illumination light including first narrowband light. The second light source system generates second illumination light including second narrowband light. The first light source system has a first semiconductor light source. The color imaging device images the internal body portion illuminated with the first or second illumination light. The color imaging device has pixels of two or more colors. Electric charge accumulated in each pixel is read out periodically as a pixel value. The controller controls the first and second light source systems such that the first and second illumination light is applied alternately to the internal body portion in a vascular observation mode. The controller puts the first semiconductor light source of the first light source system into a reduced light state without turning off the first semiconductor light source during the application with the second illumination light. The noise removal section removes a noise component from the pixel value, used for imaging of vascular information of the internal body portion, with the use of the correlation operation of the pixel values of the two or more colors, to calculate a corrected pixel value. The noise component is caused by illumination of the first semiconductor light source in the reduced light state. The image production section produces a vascular information image based on the corrected pixel value. The display section displays the vascular information image.

It is preferable that one of the first and second light source systems is alternately put into the reduced light state for a charge accumulation period of the pixel.

It is preferable that the second light source system has a second semiconductor light source. The controller puts the second semiconductor light source of the second light source system into the reduced light state without turning off the second semiconductor light source during the application of the first illumination light. The noise removal section further removes a noise component, caused by the illumination of the second semiconductor light source in the reduced light state, to calculate the corrected pixel value.

It is preferable that illumination of a first emission pattern and illumination of a second emission pattern is applied alternately in the vascular observation mode. The first emission pattern is a mixture of the first illumination light and the second illumination light in the reduced light state. The second emission pattern is a mixture of the first illumination light in the reduced light state and the second illumination light.

It is preferable that the first light source system has the first semiconductor laser for generating the first narrowband light, and a wavelength converter for generating fluorescence in a wavelength range from green to red upon excitation with the first and second narrowband light. It is preferable that the second light source system has the second semiconductor laser for generating the second narrowband light and the wavelength converter shared with the first light source system.

It is preferable that the first narrowband light has an emission peak in a blue wavelength range. It is preferable that the second narrowband light has an emission peak in a wavelength range from blue and green. It is preferable that the fluorescence is broadband light in a wavelength range from green to red. The first illumination light is a mixture of the fluorescence from the wavelength converter excited by the first narrowband light, and the first narrowband light passed through the wavelength converter. The second illumination light is a mixture of the fluorescence from the wavelength converter excited by the second narrowband light, and the second narrowband light passed through the wavelength converter.

It is preferable that the two or more colors are red, green, and blue. It is preferable that the red and green pixel values obtained under the illumination of the first emission pattern and a blue pixel value obtained under the illumination of the second emission pattern are used for producing the vascular information image.

It is preferable that the noise removal section removes the noise component, caused by the second illumination light in the reduced light state, from the green pixel value obtained under the illumination of the first emission pattern, and removes a noise component, caused by the first illumination light in the reduced state, from the blue pixel value obtained under the illumination of the second emission pattern.

It is preferable that the two or more colors are cyan, magenta, and yellow. It is preferable that magenta and yellow pixel values obtained under the illumination of the first emission pattern and a cyan pixel value obtained under the illumination of the second emission pattern are used for producing the vascular information image.

It is preferable that the noise removal section removes the noise component, caused by the second illumination light in the reduced light state, from the magenta and yellow pixel values obtained under the illumination of the first emission pattern, and removes a noise component, caused by the first illumination light in the reduced state, from the cyan pixel value obtained under the illumination of the second emission pattern.

It is preferable that the vascular information is an oxygen saturation level of hemoglobin in blood in the blood vessel, and the blood vessels in the vascular information image are color-coded in accordance with the oxygen saturation level.

It is preferable that the electronic endoscope system further includes a normal observation mode. In the normal observation mode, the internal body portion is illuminated with the first illumination light.

A method for controlling an electronic endoscope system includes an applying step, an imaging step, a producing step, and a displaying step. In the applying step, first and second illumination light is applied alternately to an internal body portion including a blood vessel. The first semiconductor light source of the first light source system is kept in a reduced light state without being turned off during the application of the second illumination light. In the imaging step, the internal body portion is imaged with a color imaging device. The color imaging device has pixels of two or more colors. Electric charge accumulated in each pixel is read out periodically as a pixel value. In the producing step, a vascular information image is produced based on the pixel value of the each color. In the displaying step, the vascular information image is displayed on a display section.

It is preferable that the second light source system has a second semiconductor light source, and the second semiconductor light source is kept in a reduced light state without being turned off during the application of the first illumination light.

It is preferable that the method further including a noise removing step. In the noise removing step, a noise component is removed from the pixel value, used for imaging of vascular information of the internal body portion, with the use of correlation operation of the pixel values of the two or more colors, to calculate a corrected pixel value. The noise component is caused by the illumination of the first semiconductor light source or the second semiconductor light source in the reduced light state. The vascular information image is produced based on the corrected pixel value.

According to the present invention, the semiconductor light source is kept turned on with its light quantity reduced even when it is supposed to be turned off. Accordingly, the overshoot, caused by the turning on of the semiconductor light source, is prevented. The noise components caused by the light from the constantly turned on semiconductor light sources are removed from the pixel values of multiple colors. Thereby, accurate vascular information image is produced.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
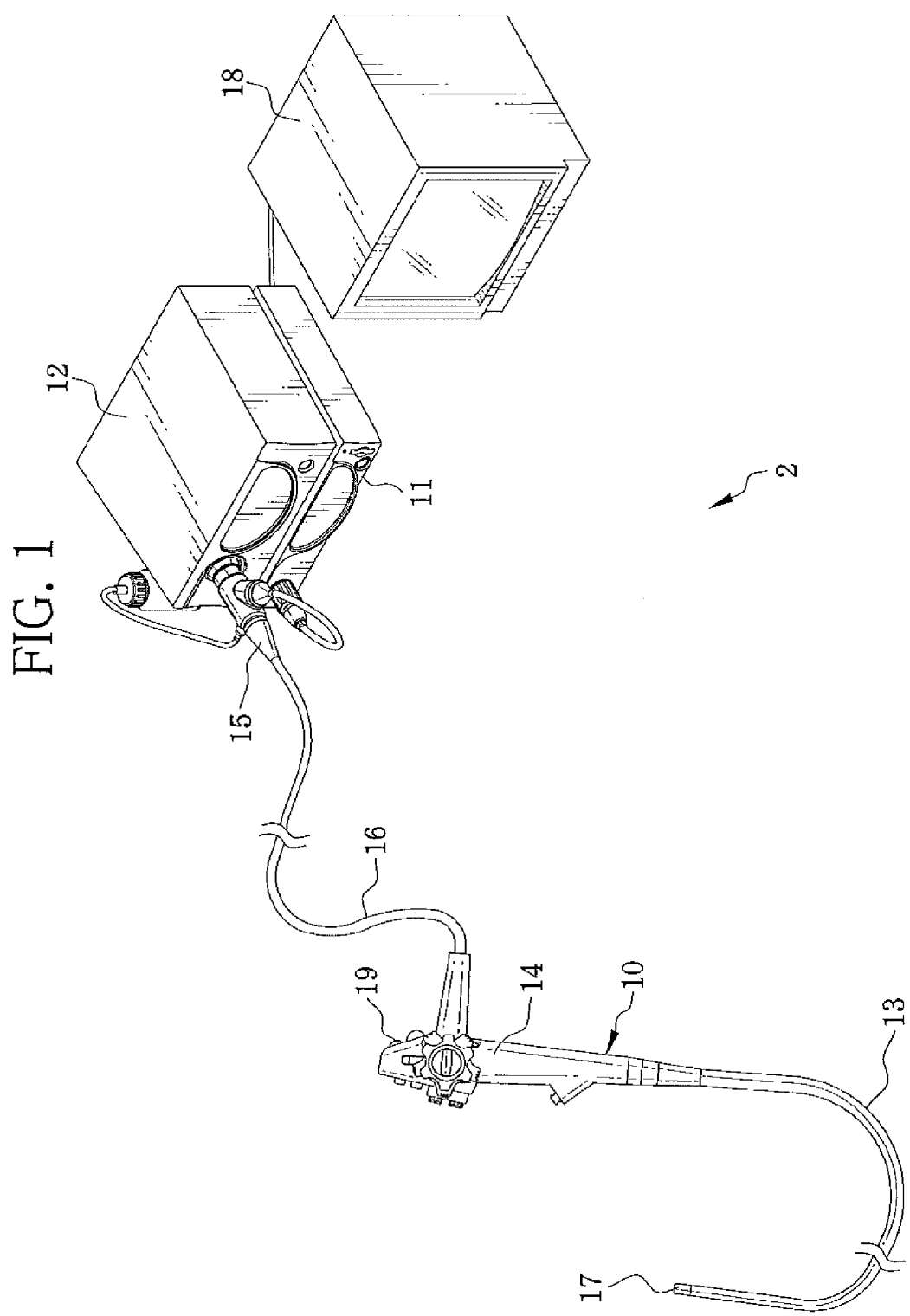
FIG. 1 is an external view of an electronic endoscope system.

In FIG. 1, an electronic endoscope system 2 is provided with an electronic endoscope 10, a processor device 11, a light source device 12, and the like. The electronic endoscope 10 has a flexible insert section 13 to be inserted into a subject (patient's body), a handling section 14 joined to a basal portion of the insert section 13, a connector 15 connected to each of the processor device 11 and the light source device 12, and a universal cord 16 connecting the handling section 14 to the connector 15.

The handling section 14 is provided with operation members, for example, an angle knob for bending a distal portion 17 of the insert section 13 in horizontal and vertical directions, an air/water button for ejecting air and/or water from an air/water nozzle, and a release button for capturing a still observation image (endoscopic image).

A forceps inlet is provided on a distal side of the handling section 14. A medical instrument such as an electric scalpel is inserted into the forceps inlet. The forceps inlet is connected to a forceps outlet provided on the distal portion 17 through a forceps channel in the insert section 13.

The processor device 11 is connected electrically to the light source device 12 and controls operation of the whole electronic endoscope system 2. The processor device 11 supplies power to the electronic endoscope 10 through a transmission cable routed through the universal cord 16 and the insert section 13. The processor device 11 controls operation of a color CCD (see FIG. 2, hereinafter simply referred to as the CCD) 33 in the distal portion 17. The processor device 11 receives an image signal outputted from the CCD 33 through the transmission cable. The processor device 11 performs various image processing steps to the image signal to produce image data. The image data is sent to a monitor 18, cable-connected to the processor device 11, and displayed as an observation image on a screen of the monitor 18.

The electronic endoscope system 2 is provided with a normal observation mode and a vascular observation mode (narrowband light mode). In the normal observation mode, an internal body portion of the subject is observed under illumination with white light. In the vascular observation mode, the white light including specific narrowband light is applied to the internal body portion to calculate vascular information of a blood vessel included in the internal body portion. The vascular information is, for example, an oxygen saturation level of hemoglobin in the blood vessel. A mode switch 19 on the handling section 14 is used for switching between the modes. When turned on, the electronic endoscope system is automatically set to the normal observation mode by a command from the processor device 11.

Figure 2:
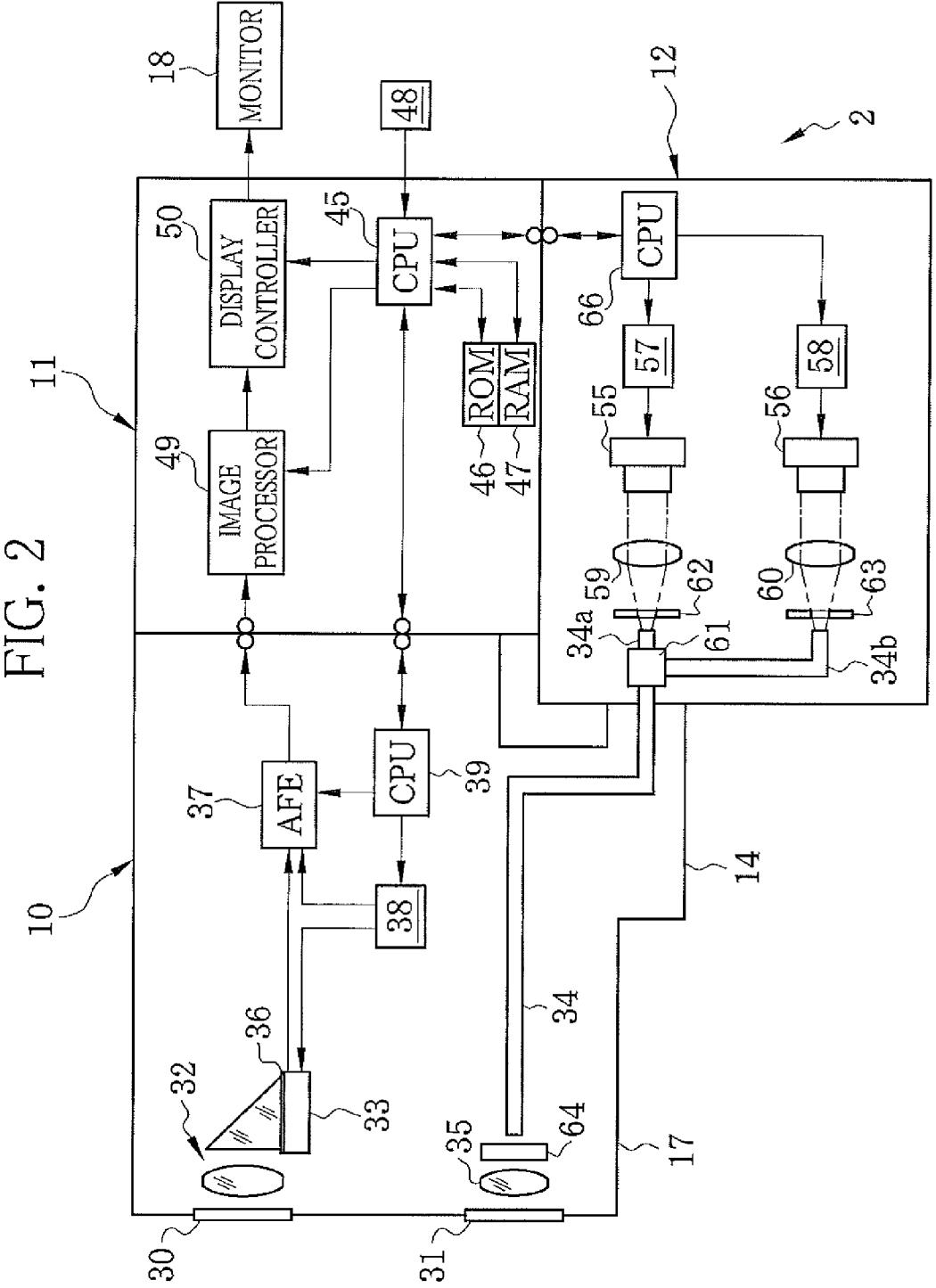
FIG. 2 is a block diagram of the electronic endoscope system.

In FIG. 2, an imaging window 30, a lighting window 31, and the like are provided on a distal end surface of the distal portion 17. Behind the imaging window 30, an objective optical system 32 composed of a lens group and a prism is disposed. A CCD 33 is disposed behind the objective optical system 32. A lighting lens 35 is attached to the lighting window 31. The lighting lens 35 applies the illumination light to the internal body portion. The illumination light from the light source device 12 is transmitted to the lighting lens 35 through a light guide 34 routed through the universal cord 16 and the insert section 13.

Figure 3:
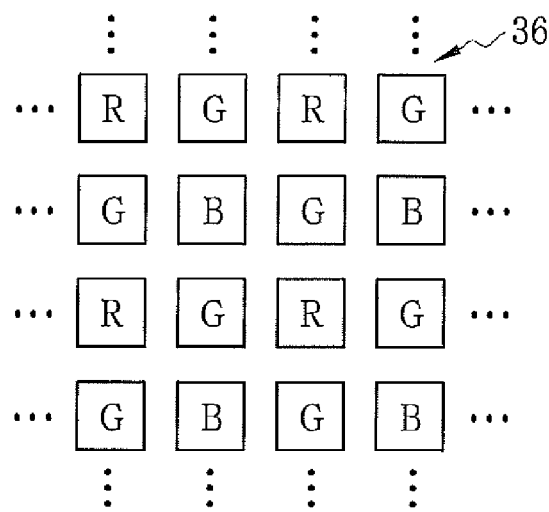
FIG. 3 is an explanatory view of a color filter with a Bayer arrangement.
Figure 4:
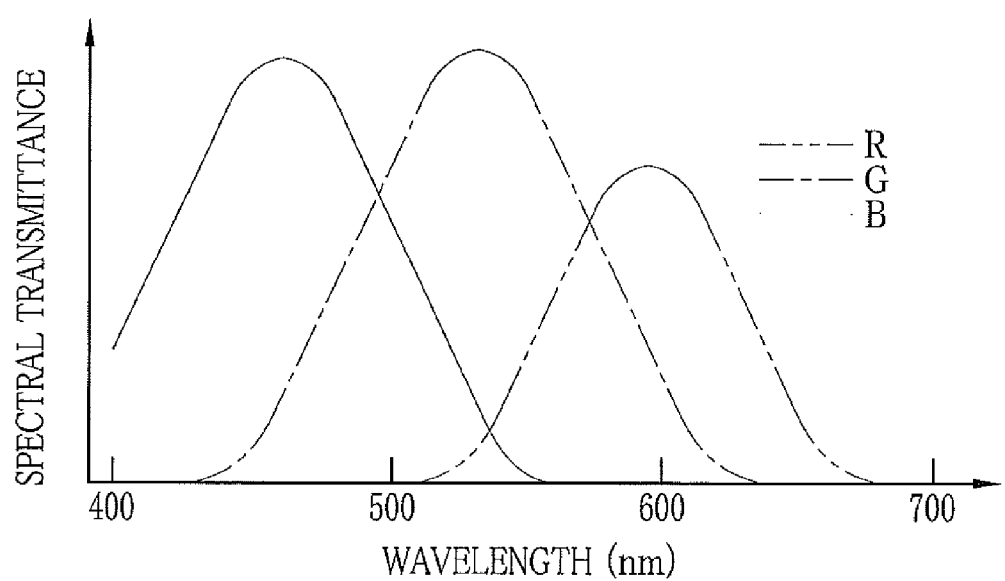
FIG. 4 is a graph showing spectral sensitivity characteristics of each of R, G, and B pixels of a color CCD.

Reflection light from the internal body portion is incident on the CCD 33 through the imaging window 30 and the objective optical system 32. The CCD 33 converts the reflection light photoelectrically into the image signal, and outputs the image signal. Red (R) pixels, green (G) pixels, and blue (B) pixels are arranged in a matrix on an imaging surface of the CCD 33. Each pixel is composed of a color filter segment and a photodiode. In this embodiment, a three primary color filter 36 of a Bayer arrangement is used (see FIG. 3). FIG. 4 shows spectral sensitivity characteristics of each of the R, G, and B pixels of the CCD 33, determined by spectral transmittance of the three primary color filter 36 and the spectral sensitivity of pixels themselves. The R pixel has a sensitivity peak at around 600 nm. The G pixel has a sensitivity peak at around 530 nm. The B pixel has a sensitivity peak at around 460 nm. Wavelength bands of the R, G, and B pixels overlap with each other. For example, both the B and G pixels are sensitive in a wavelength band of 450 nm to 530 nm.

An analog front end (AFE) 37 is composed of a correlated double sampling circuit (CDS), an automatic gain controller (AGC), and an analog/digital converter (A/D), as is well known. The CDS performs correlated double sampling to the image signal outputted from the CCD 33, to remove reset noise and amplification noise occurred in the CCD 33. Then the AGC amplifies the image signal with a gain specified by the processor device 11. Thereafter, the A/D converts the image signal into a digital image signal of a predetermined bit number. The digital image signal is inputted to an image processor 49 of the processor device 11 through a transmission cable.

A CCD driver (timing generator) 38 generates drive pulses (vertical/horizontal scan pulses, electronic shutter pulse, read-out pulse, reset pulse, and the like) for the CCD 33 and a synchronization pulse for the AFE 37. In response to the drive pulse from the CCD driver 38, the CCD 33 carries out imaging operations to output the image signal. Each section of the AFE 37 operates in response to the synchronization pulse from the CCD driver 38.

After the electronic endoscope 10 is connected to the processor device 11, a CPU 39 actuates the CCD driver 38 in response to an operation start command from a CPU 45 of the processor device 11. The CPU 39 adjusts the gain of the AGC in the AFE 37.

The CPU 45 controls the operation of the whole processor device 11. The CPU 45 is connected to each section through a data bus, an address bus, and control lines (all not shown). A ROM 46 stores various programs (OS, application programs, and the like) for controlling the operation of the processor device 11, and data (graphic data, and the like). The CPU 45 reads out the necessary programs and the data from the ROM 46 and loads them into a RAM 47 being a working memory, and runs the programs in sequence. The CPU 45 obtains information, such as text data including examination date and time, a patient's name, and a doctor's name, on an examination-by-examination basis from an operation panel of the processor device 11 or through a network, for example, LAN (local Area Network), and writes the information to the RAM 47.

An operation unit 48 is a well-known input device such as the operation panel provided on a housing of the processor device 11, a mouse, or a keyboard. The CPU 45 operates each section in response to an operation signal from the operation unit 48 or from a release button or the mode switch 19 provided on the handling section 14 of the electronic endoscope 10.

The image processor 49 performs various image processing steps such as color interpolation, white balance adjustment, gamma correction, image enhancement, image noise reduction, and color conversion to the image signal inputted from the electronic endoscope 10. The image processor 49 calculates the vascular information (oxygen saturation level) which will be described later.

A display controller 50 receives the graphic data from the ROM 46 and the RAM 47 through the CPU 45. The graphic data includes a display mask, text data, and a graphical user interface (GUI). The display mask covers an ineffective pixel area of the observation image to display only an effective pixel area. The text data includes the examination date and time, the patient's name, the doctor's name, and the current mode selected. The display controller 50 performs various display control processing steps to the image sent from the image processor 49. The display control processing steps include superimposition of the display mask, the text data, and the GUI on the image, and a drawing process for displaying the image on the screen of the monitor 18.

The display controller 50 has a frame memory (not shown) for temporarily storing the image from the image processor 49. The display controller 50 reads out the image from the frame memory and then converts the image into a video signal (component signal, composite signal, or the like) conforming to a display format of the monitor 18. Thereby, an observation image is displayed on the screen of the monitor 18.

In addition, the processor device 11 is provided with a compression circuit, a media I/F, a network I/F, and the like (all not shown). The compression circuit compresses the image with a predetermined compression format (for example, a JPEG format). The media I/F writes the compressed image to a removable medium such as a CF card, a magneto-optical disk (MO), or a CD-R. The network I/F controls transmission of various types of data to and from the network such as the LAN. The compression circuit, the media I/F, the network I/F, and the like are connected to the CPU 45 through the data bus and the like.

Figure 5:
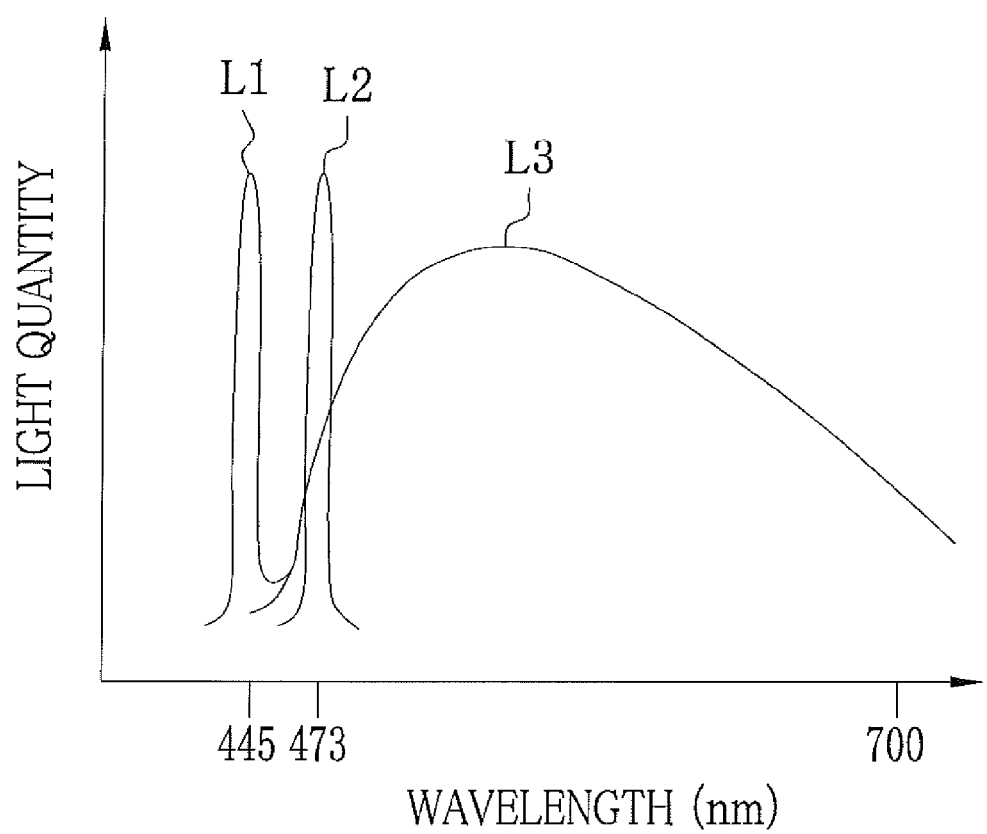
FIG. 5 is a graph showing emission spectra of first and second excitation light, and fluorescence.

The light source device 12 has a first semiconductor laser 55 and a second semiconductor laser 56. Each of the first and second semiconductor lasers 55 and 56 is a semiconductor laser diode, for example, a broad area type InGaN laser diode, an InGaNAs laser diode, or a GaNAs laser diode. As shown in FIG. 5, the first semiconductor laser 55 emits blue first excitation light L1 with a center wavelength of, for example, 445 nm. The first excitation light L1 causes (excites) a wavelength converter 64 to emit fluorescence. A part of the first excitation light L1, being the narrowband light, passes through the wavelength converter 64. The second semiconductor laser 56 emits second excitation light L2 with a center wavelength in a wavelength range from blue to green, for example, 473 nm. The second excitation light L2 causes (excites) the wavelength converter 64 to emit fluorescence, though less efficiently than the first excitation light L1. A part of the second excitation light L2, being the narrowband light, passes through the wavelength converter 64, and is used for calculating the oxygen saturation level of hemoglobin in the blood vessel. A first light source system is composed of the first semiconductor laser 55 and the wavelength converter 64. A second light source system is composed of the second semiconductor laser 56 and the wavelength converter 64.

The first and second semiconductor lasers 55 and 56 are driven by light source drivers 57 and 58, respectively. Condenser lenses 59 and 60 gather light from the first and second semiconductor lasers 55 and 56 to allow the light to be incident on light guides 34a and 34b, respectively. The light guides 34a and 34b are disposed on exit end sides of the first and second semiconductor lasers 55 and 56, respectively. The light guides 34a and 34b are connected to a single light guide 34 through a coupler 61. A variable aperture stop 62 is disposed between the condenser lens 59 and the light guide 34a. A variable aperture stop 63 is disposed between the condenser lens 60 and the light guide 34b. The variable aperture stops 62 and 63 control light quantities of the light incident on the light guides 34a and 34b, respectively. Instead of the coupler 61, the first and second semiconductor lasers 55 and 56 may be provided with their respective light guides to transmit the light separately to the lighting window 31.

The wavelength converter 64 is a glass plate on which several kinds of phosphor are applied or dispersed. The phosphor absorb a part of the blue first excitation light L1 from the first semiconductor laser 55 and a part of the cyan second excitation light L2 from the second semiconductor laser 56, to emit fluorescence in a wavelength range from green to red. Note that the wavelength converter 64 emits a small quantity of blue light. However, the color of the fluorescence emitted from the phosphor is referred to as "green to red". When the first semiconductor laser 55 is turned on, the fluorescence ("L3" in FIG. 5) in the wavelength range from green to red and the blue first excitation light L1 left unabsorbed is mixed to generate the white light. The white light is applied to the internal body portion through the lighting window 31. Examples of the phosphor include YAG fluorescent substances or BAM ($BaMgAl_{10}O_{17}$) fluorescent substances. The phosphor sold under the product name Micro White (or MW) (registered trademark) can be used.

As shown in FIG. 4, only the B pixel is sensitive to the reflection light of the first excitation light L1 with the center wavelength of 445 nm. The B and G pixels are sensitive to the reflection light of the second excitation light L2 with the center wavelength of 473 nm. Because the fluorescence L3 is the light in a broad range of approximately 450 nm to 700 nm, all of the R, G, and B pixels are sensitive to the fluorescence L3. Note that the output of the B pixel is small.

A CPU 66 of the light source device 12 communicates with the CPU 45 of the processor device 11. The CPU 66 separately controls ON/OFF of the first semiconductor laser 55 through the light source driver 57 and that of the second semiconductor laser 55 through the light source driver 58. The CPU 66 separately controls the light quantity of the first semiconductor laser 55 through the variable aperture stop 62 and that of the second semiconductor laser 56 through the variable aperture stop 63.

When the normal observation mode is selected, the CPU 45 controls the light source driver 57 through the CPU 66 to turn on only the first semiconductor laser 55. Namely, the illumination light applied to the internal body portion is the white light, being a mixture of the fluorescence L3, emitted from the wavelength converter 64 excited by the first excitation light L1 with the center wavelength of 445 nm from the first semiconductor laser 55, and the first excitation light L1 passed through the wavelength converter 64.

Figure 6:
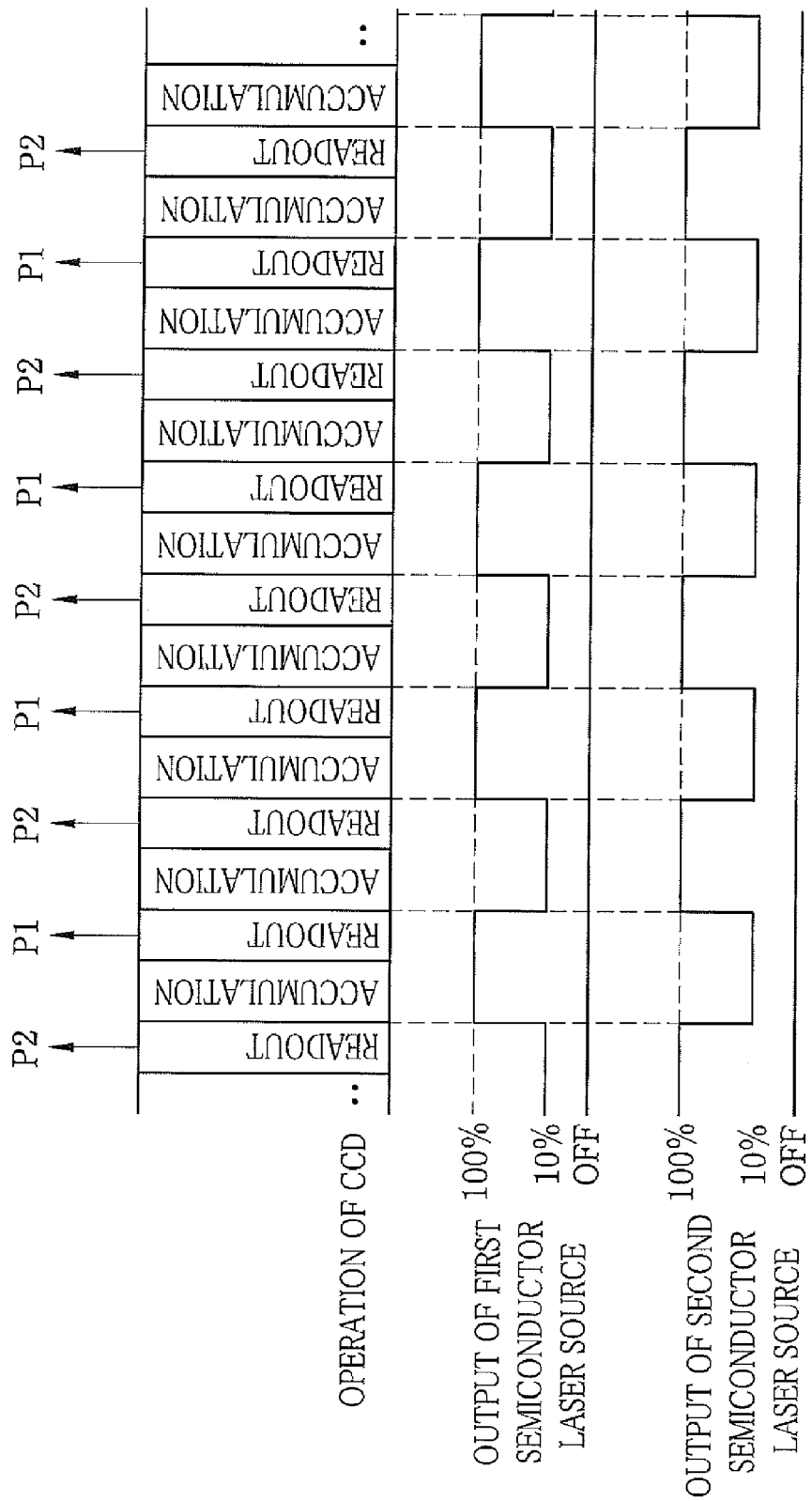
FIG. 6 is a timing chart showing respective operations of the color CCD, and first and second semiconductor lasers.

When the vascular observation mode is selected, the CPU 45 controls the light source drivers 57 and 58 through the CPU 66 so as to allow one of the lasers 55 and 56 to emit light in a full light state, at 100% rated output (light quantity), and the other to emit light in a reduced light state, for example, at 10% rated output, as shown in FIG. 6. Then, each of the lasers 55 and 56 switches between the full and reduced light states on a unit by unit basis of accumulation and readout periods. In other words, in the vascular observation mode, both the lasers 55 and 56 are kept turned on without being turned off. This prevents overshoot because the overshoot occurs due to turning on the light source after turning it off. Note that each or one of the lasers 55 and 56 may emit light at 100% rated output only during the accumulation periods. During the readout periods between the accumulation periods, each or one of the lasers 55 and 56 may emit light at 10% rated output.

Figure 7A:
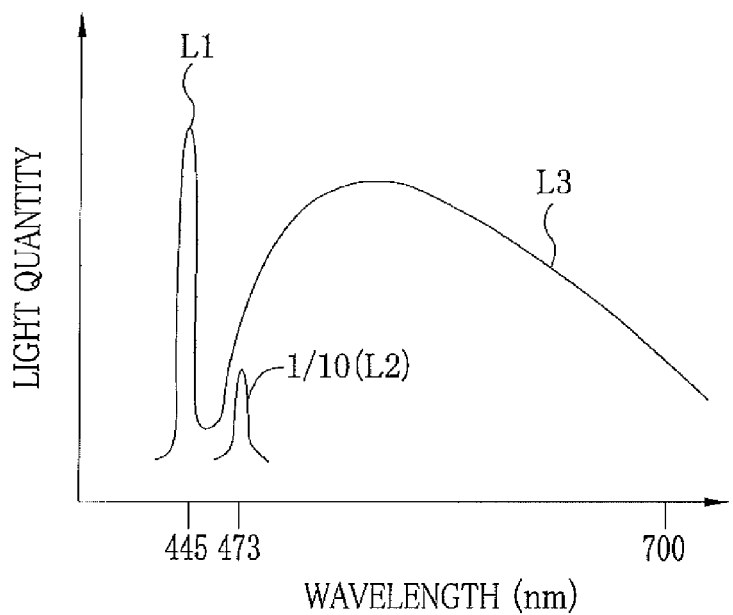
FIG. 7A is a graph showing emission spectra of a first emission pattern.
Figure 7B:
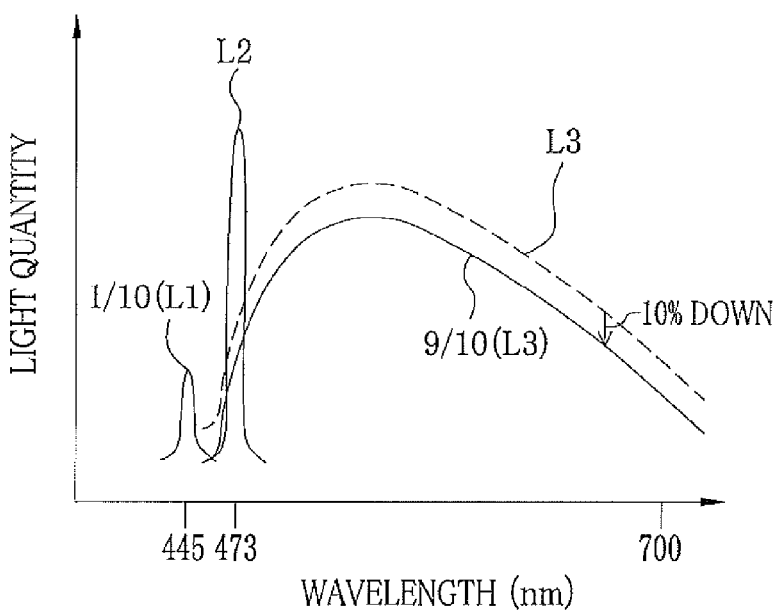
FIG. 7B is a graph showing emission spectra of a second emission pattern.

As shown in FIGS. 7A and 7B, during the above-described emission control of the lasers 55 and 56, the first and second emission patterns are repeated alternately. The first and second emission patterns are different from each other in emission intensity. As shown in FIG. 7A, in the first emission pattern, the white light, being the mixture of the first excitation light L1 at 100% rated output, the second excitation light "⅒(L2)" at 10% rated output, and the fluorescence L3, is applied to the internal body portion. The fluorescence L3 refers to the light emitted from the wavelength converter 64 excited by the first excitation light L1 and the second excitation light ⅒(L2). As shown in FIG. 7B, in the second emission pattern, the substantially white light, being the mixture of the first excitation light "⅒(L1)" at 10% rated output, the second excitation light L2 at 100% rated output, and the fluorescence "⁹⁄₁₀(L3)", is applied to the internal body portion. The fluorescence "⁹⁄₁₀(L3)" refers to the light emitted from the wavelength converter 64 excited by the first excitation light ⅒(L1) and the second excitation light L2. The wavelength converter 64 absorbs the first excitation light L1 at higher absorptivity than the second excitation light L2. Accordingly, "9/10(L3)" represents that the emission intensity of the fluorescence L3 in the second emission pattern decreases by 10% compared to that in the first emission pattern.

Figure 8:
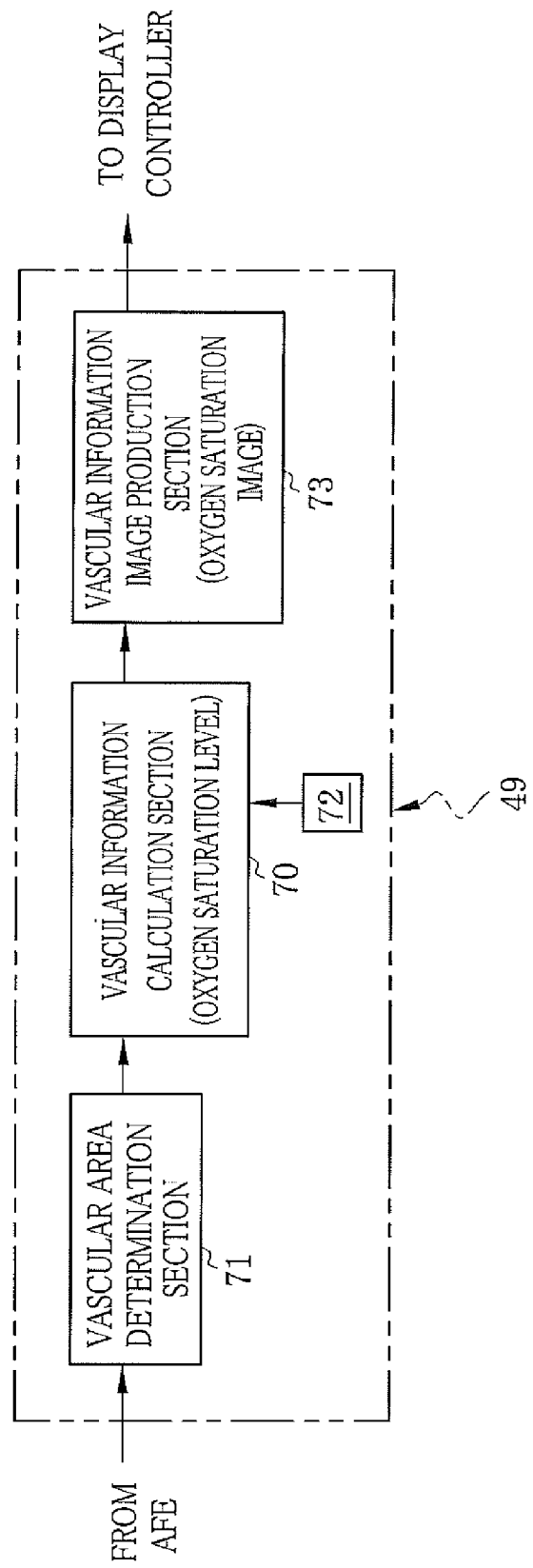
FIG. 8 is a block diagram of an image processor.

In FIG. 8, the image processor 49 is provided with a vascular area determination section 71, a vascular information calculation section 70, and a vascular information image production section 73. The vascular area determination section 71 analyzes an image inputted from the AFE 37. For example, the vascular area determination section 71 obtains or refers to a difference in luminance value between a vascular area and a non-vascular area to determine (extract) the vascular area in (from) the image. The vascular area determination section 71 outputs information of the vascular area extracted, together with an image, to the vascular information calculation section 70. The vascular information calculation section 70 calculates the vascular information, for example, the oxygen saturation level of hemoglobin in a blood vessel. The vascular information calculation section 70 calculates the oxygen saturation level based on two frames of images P1 and P2 (see FIG. 6) of the internal body portion captured successively in the vascular observation mode. The image P1 is captured under illumination light of the first emission pattern. The image P2 is captured under illumination light of the second emission pattern. The illumination light of the first emission pattern and that of the second emission pattern is applied to the internal body portion alternately. Additionally, a blood flow rate in the blood vessel can be measured. Furthermore, a position (depth) of the blood vessel can be located or determined, and information on the blood vessel located can be obtained.

Figure 9:
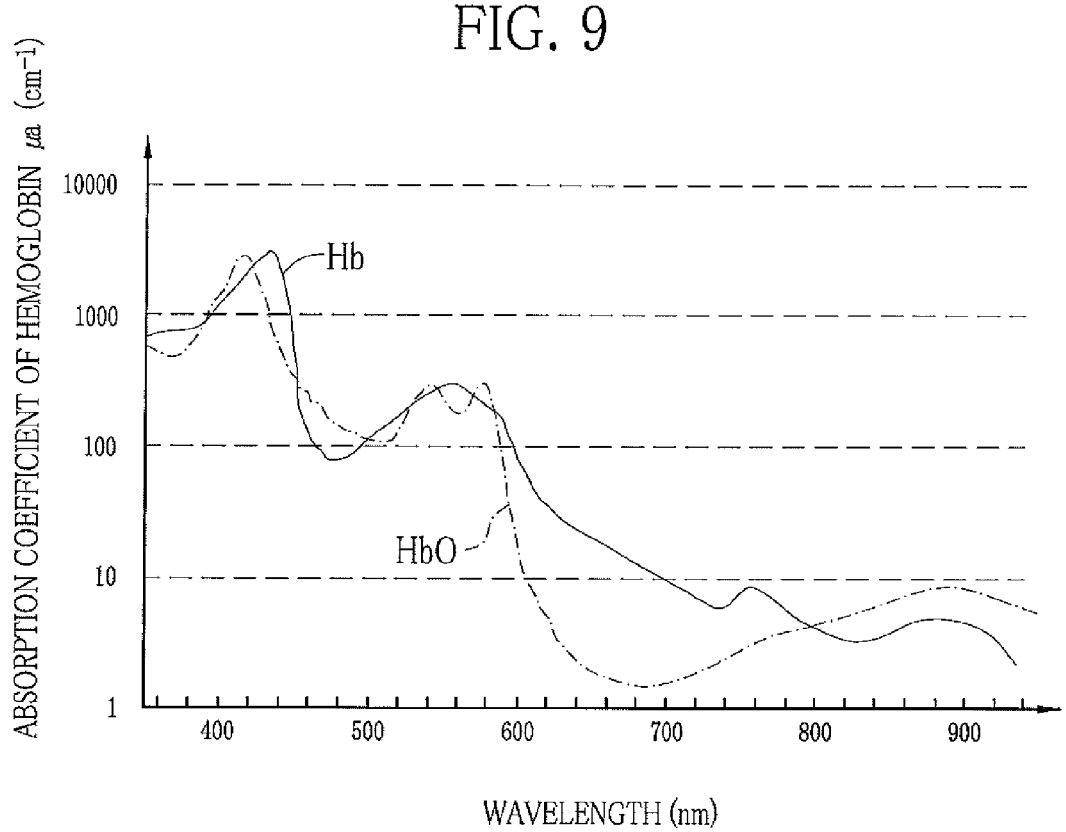
FIG. 9 is a graph showing absorption characteristics of oxyhemoglobin and deoxyhemoglobin.

As shown in FIG. 9, an absorption coefficient pa of the hemoglobin varies with a wavelength of the illumination light. The absorption coefficient μa represents absorbance or magnitude of light absorbed by the hemoglobin. The absorption coefficient is a coefficient of an expression $I_0\exp(-\mu a \times x)$ representing attenuation of the light applied to the hemoglobin. Note that "$I_0$" denotes intensity of the illumination light, and "x" (unit: cm) denotes the depth of the blood vessel from the surface of the internal body portion.

Deoxyhemoglobin Hb not combined with oxygen differs from oxyhemoglobin HbO combined with the oxygen in light absorption properties. An absorption coefficient pa of the deoxyhemoglobin is different from that of the oxyhemoglobin except at isosbestic points. The isosbestic point is a point of intersection of the absorption coefficients pa of the deoxyhemoglobin and oxyhemoglobin, at which the absorption coefficients pa of the deoxyhemoglobin and the oxyhemoglobin have the same value.

When there is a difference in absorption coefficient pa between the deoxyhemoglobin and the oxyhemoglobin, intensities of the reflection light from the blood vessel vary even if light of a constant wavelength and constant intensity is applied to the blood vessel. When light of different wavelengths and constant intensity is applied to the blood vessel, the intensities of the reflection light still vary because the absorption coefficient pa varies with the wavelength. Accordingly, a ratio between the oxyhemoglobin and the deoxyhemoglobin in the blood vessel, that is, the information of oxygen saturation level is obtained or determined by analyzing images captured under the illumination including two or more wavelength bands of the narrowband light.

The vascular information calculation section 70 has a frame memory (not shown) for temporarily storing the image P1 captured under the illumination light of the first emission pattern and the image P2 captured under the illumination of the second emission pattern in the vascular observation mode. The vascular information calculation section 70 reads out each of the images P1 and P2 from the frame memory. The vascular information calculation section 70 uses the pixel values of the vascular area, determined by the vascular area determination section 71, of each of the images P1 and P2 to carry out various calculations. For example, the vascular information calculation section 70 calculates a ratio or a difference in pixel values between the images P1 and P2 to obtain an image parameter.

By way of example, calculation of the oxygen saturation level using the first image P1 captured under the illumination light of the first emission pattern and the second image P2 captured under the illumination light of the second emission pattern is described.

The R, G, and B pixel values "r1", "g1", and "b1" of the first image P1 are obtained from the reflection light of the illumination light L1 to L3. Referring to the spectral transmittance of each of the R, G, and B pixels of the CCD 33 shown in FIG. 4 and the spectral intensity characteristic of each of the illumination light L1 to L3 shown in FIGS. 7A and 7B, each of the R pixel value r1, the G pixel value g1, and the B pixel value b1 of the first image P1 is expressed using at least one of the illumination light L1 to L3, as shown in expressions (1) to (3) below.

$$r1 = L3 \tag{1}$$

$$g1 = {}^{1}\!/\!{}_{10}(L2) + L3 \tag{2}$$

$$b1 = L1 + {}^{1}\!/\!{}_{10}(L2) + L3 \tag{3}$$

The second excitation light L2 (center wavelength: 473 nm) of the first emission pattern is at 10% rated output, so the L2 is multiplied by $\frac{1}{10}$. Similarly, the R pixel value r2, the G pixel value g2, and the B pixel value b2 of the second image P2 are expressed using at least one of the illumination light L1 to L3, as shown in expressions (4) to (6) below.

$$r2 = {}^{9}\!/\!{}_{10}(L3) \tag{4}$$

$$g2 = L2 + {}^{9}\!/\!{}_{10}(L3) \tag{5}$$

$$b2 = {}^{1}\!/\!{}_{10}(L1) + L2 + {}^{9}\!/\!{}_{10}(L3) \tag{6}$$

The vascular information calculation section 70 calculates a ratio "b2/g1" (a ratio between the B pixel value b2 of the second image P2 and the G pixel value g1 of the first image P1), relative to the corresponding pixels in the first and second images P1 and P2, and a ratio "r1/g1" (a ratio between the R pixel value r1 and the G pixel value g1 of the first image P1) as the image parameters.

Conventionally, to calculate the oxygen saturation level of the hemoglobin in the blood vessel, two frames of images are obtained successively with one of the lasers 55 and 56 turned on and the other turned off alternately. Namely, one of the lasers 55 and 56 is used in each unit of the accumulation and readout periods. In this embodiment, to prevent the overshoot due to turning on and off the first and second semiconductor lasers 55 and 56, the first and second images P1 and P2 are obtained without turning off the lasers 55 and 56. In other words, a component, of the pixel value of each of the R, G, and B pixels in each of the images P1 and P2, corresponding to the light of 10% rated output is a noise component. The vascular information calculation section 70 performs correlation operation of the pixel values of the corresponding pixels in the images P1 and P2 to remove the noise component. Then, the vascular information calculation section 70 calculates an image parameter.

As described above, the B pixel value b2 of the second image P2 includes $\frac{1}{10}(L1)$ being the noise component. In calculating the oxygen saturation level, the component $\frac{9}{10}(L3)$ of the fluorescence L3 is also regarded as the noise component. First, to remove the noise component $\frac{1}{10}(L1)$, the G pixel value g1 of the first image P1 is subtracted from the B pixel value b1 of the first image P1, and then the difference is multiplied by $\frac{1}{10}$. An expression (7) is obtained from the expressions (2) and (3).

$$\frac{1}{10}(b1-g1)=\frac{1}{10}[L1+\frac{1}{10}(L2)+L3-\{\frac{1}{10}(L2)+L3\}]$$
$$=\frac{1}{10}(L1) \qquad (7)$$

To remove the noise component $\frac{9}{10}(L3)$, the R pixel value r2 of the second image P2 is used. From the expressions (4), (6), and (7), a corrected B pixel value b2', with the noise component removed, of the second image P2 is obtained with an expression (8). Thus, a component corresponding to the second excitation light L2 with the center wavelength of 473 nm is extracted.

$$b2'=b2-\frac{1}{10}(b1-g1)-r2=\frac{1}{10}(L1)+L2+\frac{9}{10}(L3)-\frac{1}{10}(L1)-\frac{9}{10}(L3)=L2 \qquad (8)$$

The G pixel value g1 of the first image P1 includes $\frac{1}{10}(L2)$ being a noise component. To remove the noise component $\frac{1}{10}(L2)$, the R pixel value r2 of the second image P2 is subtracted from the G pixel value g2 of the second image P2, and then the difference is multiplied by $\frac{1}{10}$. An expression (9) is obtained from the expressions (4) and (5).

$$\frac{1}{10}(g2-r2)=\frac{1}{10}\{L2+\frac{9}{10}(L3)-\frac{9}{10}(L3)\}=\frac{1}{10}(L2) \qquad (9)$$

From the expressions (2) and (9), a corrected G pixel value g1', with the noise component removed, of the first image P1 is obtained with an expression (10).

$$g1'=g1-\frac{1}{10}(g2-r2)=\frac{1}{10}(L2)+L3-\frac{1}{10}(L2)=L3 \qquad (10)$$

Thus, a component corresponding to the fluorescence L3 is extracted using the expression (10). The R pixel value r1 of the first image P1 does not include a noise component, so the correlation operation is not performed. The vascular information calculation section 70 uses the pixel value r1 and the corrected pixel values b2' and g1' to calculate the image parameters (b2'/g1' and r1/g1').

Note that before calculating the difference between the R, G, and B pixel values as shown in the expressions (7) to (10), each of the R, G, and B pixel values is multiplied by a predetermined correlation coefficient. The correlation coefficient is determined in advance based on the spectral transmittance of each of the R, G, and B pixels of the CCD 33 in FIG. 4, and the spectral intensity characteristics of each of the illumination light L1 to L3 in FIG. 5. The correlation coefficient is set such that the noise component is removed by calculating the difference between the R, G, and B pixel values. For example, when a spectral sensitivity ratio between the G pixel value and the R pixel value is 1.25 (G/R=1.25) relative to the fluorescence L3, the R pixel value r2 is multiplied by 1.25.

Figure 10:
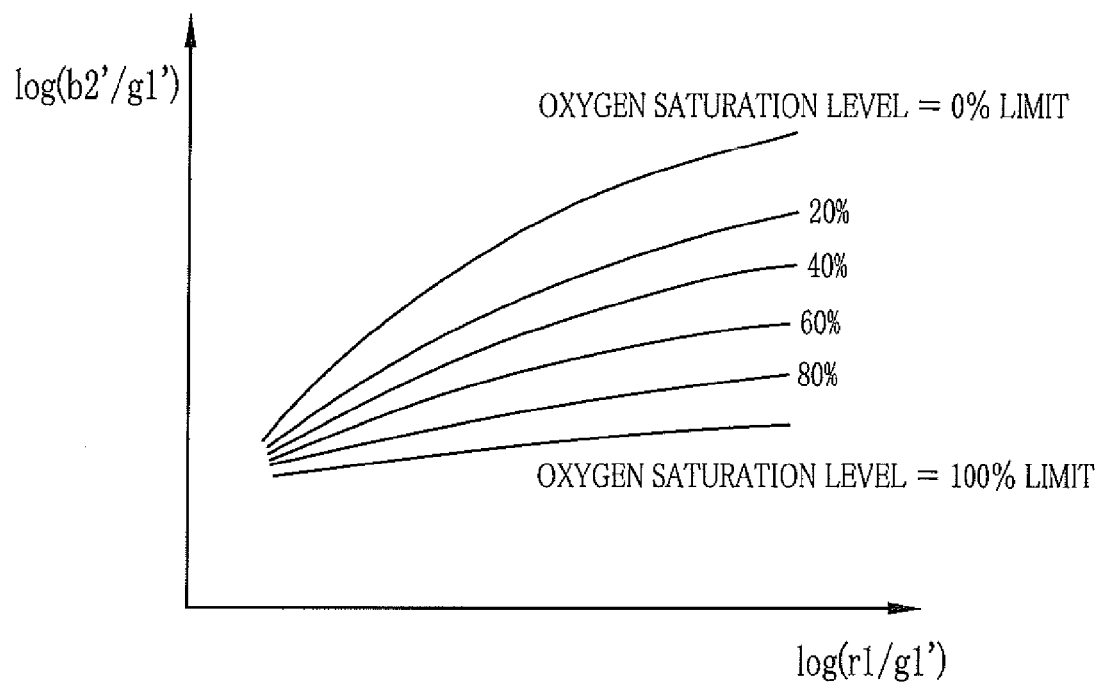
FIG. 10 is an example of reference data.

As shown in FIG. 10, reference data 72 shows relation between the image parameter and the oxygen saturation level in a form of a function or a data table. The relation between the image parameter and the oxygen saturation level is determined in advance by an experiment or the like. A signal ratio b2'/g1' increases as a signal ratio r1/g1' increases, namely, a contour line "oxygen saturation level=0% limit" extends or slides up diagonally. This is because there is a correlation between the signal ratio r1/g1' and blood volume. The blood volume increases as the signal ratio r1/g1' increases. Of the signals b2', g1', and r1, the increase in the blood volume most decreases the signal value of the green signal g1'. An amount of the signal value of the blue signal b2' decreased by the increase in the blood volume is second to that of the green signal g1'.

This is because the absorption coefficient of a wavelength component of 540 nm to 580 nm included in the G signal g1' is higher than that of a wavelength component of approximately 470 nm included in the B signal b2' (see FIG. 9). Accordingly, in the signal ratio b2'/g1', the decrease in the signal value g1' (denominator) is greater than the decrease in the signal value b2' (nominator), as the blood volume increases. In other words, the signal ratio b2'/g1' increases as the blood volume increases.

The vascular information calculation section 70 substitutes the image parameter into the function to calculate the oxygen saturation level corresponding to the image parameter, or retrieves the oxygen saturation level corresponding to the image parameter from the data table. The oxygen saturation level calculated or obtained (referred to as the calculation result) is outputted to the vascular information image production section 73.

Based on a color map for displaying the calculation result in pseudo color, the vascular information image production section 73 produces a vascular information image (in this embodiment, an oxygen saturation image) reflecting or representing the calculation result of the vascular information calculation section 70. The oxygen saturation image is an image of the oxygen saturation level obtained by the vascular information calculation section 70 with the use of the reference data 72. To produce a pseudo color image, the color map assigns, for example, cyan to an area with a relatively low oxygen saturation level, magenta to an area with a medium oxygen saturation level, and yellow to an area with a high oxygen saturation level in a vascular image.

Next, an operation of the electronic endoscope system 2 of the above-described configuration is described. Patient information is inputted and the start of the examination is commanded using the operation unit 48. Then the insert section 13 of the electronic endoscope 10 is inserted into the subject (patient's body). While being illuminated with the illumination light from the light source device 12, an observation image of the internal body portion is captured with the CCD 33. The observation image is displayed on the monitor 18, and observed.

To be more specific, the image signal outputted from the CCD 33 is subjected to various processing steps in each section of the AFE 37. Then, the image signal is inputted to the image processor 49. The image processor 49 performs various image processing steps to the image signal to produce the image of the internal body portion. The image is inputted to the display controller 50. The display controller 50 performs various display control processing steps in accordance with the graphic data. Thereby, the observation image is displayed on the monitor 18.

When the insert section 13 of the electronic endoscope 10 is inserted into the subject, a normal observation mode is selected to illuminate the internal body portion with the white light. Thereby, a wide view is ensured while the insert section 13 is inserted. When a lesion requiring careful observation is found and it is necessary to obtain its oxygen saturation level, the vascular observation mode is selected. When necessary, a still image of the lesion is captured with the operation of a release button provided on the electronic endoscope 10. When a treatment is needed, a medical instrument is inserted into the forceps channel of the electric endoscope 10 to remove the lesion or to give medicine to the lesion.

In the normal observation mode, in response to the command of the CPU 45, the CPU 66 turns on only the first semiconductor laser 55 to apply the white light, being the mixture of the first excitation light L1 and the fluorescence L3, to the internal body portion through the lighting window 31.

Figure 11:
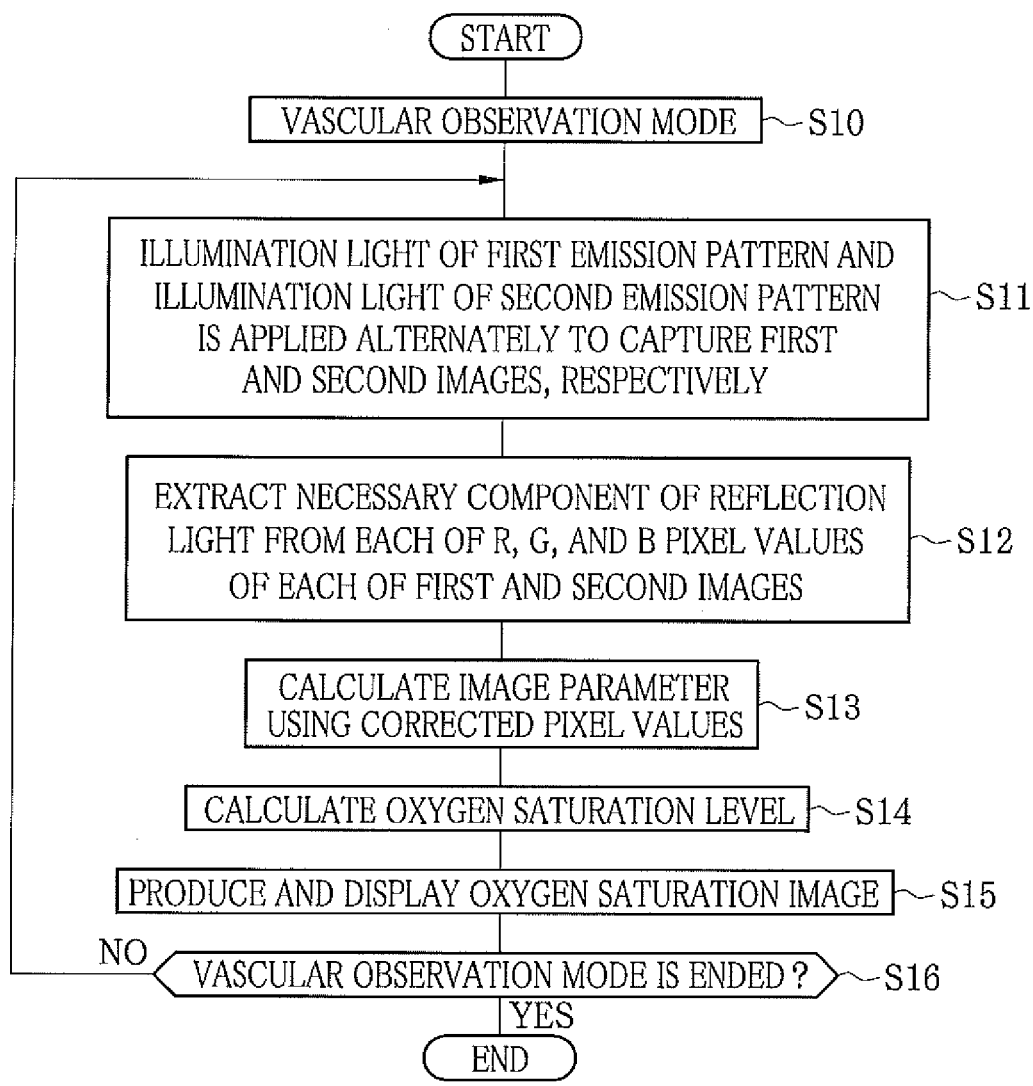
FIG. 11 is a flowchart showing a procedure in a vascular observation mode.

On the other hand, as shown in S10 of FIG. 11, when the vascular observation mode is selected using the mode switch 19, the CPU 66 puts one of the lasers 55 and 56 into 100% rated output (full light state), and the other into 10% rated output (reduced light state), for example. Each of the lasers 55 and 56 switches between the full and reduced light states alternately and repeatedly on a unit by unit basis of the accumulation and readout periods. Namely, one of the lasers 55 and 56 is put into the reduced light state while the other is put into the full light state for the unit of the accumulation and readout periods. Thereby, the illumination of the first emission pattern and that of the second emission pattern is applied alternately to the internal body portion (see FIGS. 7A and 7B). The CCD 33 outputs the first image P1 captured under the illumination of the first emission pattern, and the second image P2 captured under the illumination of the second emission pattern (S11).

In the image processor 49, first, the vascular area determination section 71 determines the vascular area. Then, the vascular information calculation section 70 performs the correlation operation to remove the noise components from the respective R, G, B pixel values in each of the vascular areas in the first and second images P1 and P2. Thereby, reflection light component(s) of the specific illumination light is extracted (S12). Thereafter, the image parameter is calculated using the corrected pixel values with the noise component removed by the correlation operation (S13). Based on the reference data 72, the oxygen saturation level of the hemoglobin in the blood vessel is calculated (S14). Based on the calculation result of the oxygen saturation level, the vascular information image production section 73 produces the oxygen saturation image in which the blood vessels are color-coded according to their oxygen saturation levels, and the oxygen saturation image is displayed on the monitor 18 (S15). The above-described steps are repeated until the normal observation mode is selected using the mode switch 19 (YES in S16).

As described above, in the present invention, when the two types of illumination light each including the specific narrowband light are applied alternately from the respective first and second semiconductor lasers 55 and 56, each of the lasers 55 and 56 is switched alternately between the full and reduced light states without being turned off. The two images P1 and P2 are obtained under the illumination of both the semiconductor lasers 55 and 56. To extract a necessary component, the noise component is removed using the correlation operation of the R, G, and B pixel values of each of the images P1 and P2. Thereby, the overshoot of each of the outputs of the lasers 55 and 56 due to turning on and off is prevented. Problems resulting from the overshoot are also prevented.

In particular, when the light quantity of the illumination light is unstable due to the overshoot, accuracy of the image parameter calculated using the pixel values of the images P1 and P2 cannot be maintained. This reduces reliability of the calculation result of the oxygen saturation level. The present invention, on the other hand, prevents the overshoot and makes the light quantity stable, which improves the reliability of the calculation result of the oxygen saturation level.

The B and G pixels of the CCD 33 are sensitive to the reflection light of the second excitation light L2 with the center wavelength of 473 nm. All of the R, G, and B pixels are sensitive to the reflection light of the fluorescence L3. Namely, each of the B and G pixel values includes the component corresponding to the second excitation light L2. Each of the R, G, and B pixel values includes the component corresponding to the fluorescence L3. This enables removal of the noise components with the use of the correlation operation and extraction of only the specific components. The correlation operation can be performed when a wavelength band of one of the illumination light overlaps with the sensitive areas of two of the R, G, and B pixels, because the spectral sensitivity characteristics of each pixel is well-known.

In the above embodiment, by way of example, the corrected G pixel value $g1'$ of the first image P1 and the corrected B pixel value $b2'$ of the second image P2 are used for the correlation operation. Alternatively, as shown in an expression (11) below, the R pixel value $r2$ of the second image is subtracted from the G pixel value $g2$ of the second image P2 to extract the component corresponding to the second excitation light L2 with the center wavelength of 473 nm.

$$g2'=g2-r2=L2+9/10(L3)-9/10(L3)=L2 \quad (11)$$

Alternatively, as shown in an expression (12), the G pixel value $g1$ of the first image P1 is subtracted from the B pixel value $b1$ of the first image P1 to extract the component corresponding to the first excitation light L1 with the center wavelength of 445 nm.

$$b1'=b1-g1=L1+1/10(L2)+L3-\{1/10(L2)+L3\}=L1 \quad (12)$$

The vascular information is not limited to the oxygen saturation level of the above embodiment. The vascular information may be the blood volume in a blood vessel. The blood volume can be expressed based on a ratio $r1/g1'$. The vascular information may be vascular images (visible images of blood flow in blood vessels) of the superficial and middle mucosal layers. The vascular images are produced using the $b2'$, the $b1'$ obtained with the expression (12), and the $g2'$ obtained with the expression (11) and displayed.

Figure 12:
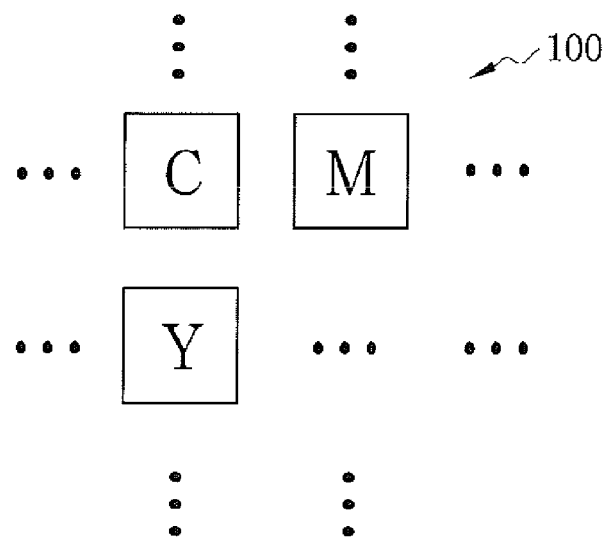
FIG. 12 is an explanatory view showing a color filter provided on a complementary color CCD.

In the above embodiment, the CCD 33 with the three primary color filter (R, G, and B) 36 of an additive color system is used. Instead, a complementary color CCD with a three primary color filter (C, M, and Y) 100 of a subtractive color system shown in FIG. 12 may be used.

Figure 13:
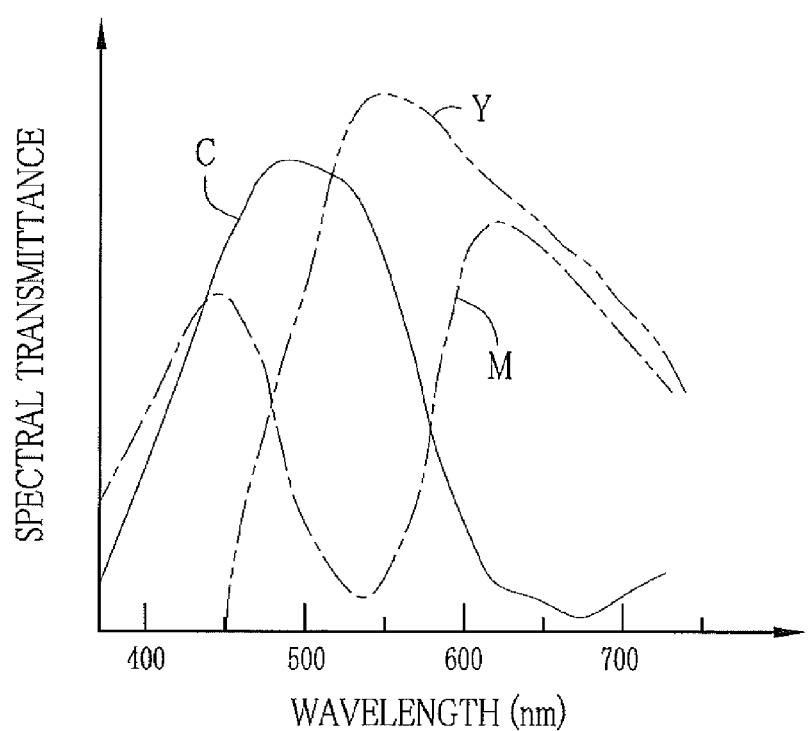
FIG. 13 is a graph showing spectral transmittance of C, M, and Y color filter segments of the color filter.

As shown in FIG. 13, a C (cyan) color filter segment has high transmittance in the blue and green wavelength bands, while having extremely low transmittance in the red wavelength band. An M (magenta) color filter segment has high transmittance in the blue and red wavelength bands, while having extremely low transmittance in the green wavelength band. A Y (yellow) color filter segment has high transmittance in a wavelength band of 450 nm or more, while having extremely low transmittance in a wavelength band less than 450 nm.

Referring to the first and second emission patterns shown in FIGS. 7A and 7B in the vascular observation mode, and the transmission characteristics of the C, M, and Y color filter segments shown in FIG. 13, a C pixel provided with the C color filter segment is sensitive to the first excitation light L1, the second excitation light L2, and a green component of the fluorescence L3. An M pixel provided with the M color filter segment is sensitive to the first excitation light L1, the second excitation light L2, and a red component of the fluorescence L3. A Y pixel provided with the Y color filter segment is sensitive to the second excitation light L2 and the green and red components of the fluorescence L3.

Accordingly, the pixel values C1, M1, and Y1 of the first image P1 and the pixel values C2, M2, and Y2 of the second image P2, outputted from the complementary color CCD, are expressed as follows.

$$C1 = L1 + 1/10(L2) + \alpha(L3) \quad (X1)$$

$$M1 = L1 + 1/10(L2) + \beta(L3) \quad (X2)$$

$$Y1 = 1/10(L2) + L3 \quad (X3)$$

$$C2 = 1/10(L1) + L2 + \alpha \times 9/10(L3) \quad (X4)$$

$$M2 = 1/10(L1) + L2 + \beta \times 9/10(L3) \quad (X5)$$

$$Y2 = L2 + 9/10(L3) \quad (X6)$$

In the expressions, the $\alpha(<1)$ represents a percentage of a component (mostly the green component), of the fluorescence L3, passing the C color filter segment. The $\beta(<1)$ represents a percentage of a component (mostly the red component), of the fluorescence L3, passing the M color filter segment.

When the complementary color CCD is used, the pixel values M1 and Y1 of the first image P1 and the pixel value C2 of the second image P2 are converted into R, G, and B values. The oxygen saturation level is calculated based on the converted R, G, and B values. Note that, before the conversion into the R, G, and B values, a noise component, being the component of the light of the 10% rated output for preventing the overshoot, is removed from the pixel values M1, Y1, and C2.

The pixel value C2 of the second image P2 includes the noise component $1/10(L1)$. In the calculation of the oxygen saturation level, "$\alpha \times 9/10(L3)$", being the component of the fluorescence L3, is also regarded as the noise component. As shown below, by removing the noise components $1/10(L1)$ and $\alpha \times 9/10(L3)$ from the pixel value C2, a corrected pixel value C2' having only the component corresponding to the second excitation light L2 is obtained.

$$C2' = C2 - 1/10(L1) - \alpha \times 9/10(L3) = L2$$

Note that, for the L3, a value obtained from the expressions (X3) and (X6) is used as shown below.

$$L3 = 90/91(Y1) \quad (X7)$$

For the L1, a value obtained from the expressions (X1), (X4), and (X7) is used as shown below.

$$L1 = 100/99\{(C1 - 1/10(C2)) - 9/10(Y1)\}$$

On the other hand, the pixel value M1 of the first image P1 includes the noise component $1/10(L2)$, so the noise component $1/10(L2)$ is removed from the pixel value M1. Thereby, a corrected pixel value M1', having the component corresponding to the first excitation light L1 and the component corresponding to the fluorescence $\beta(L3)$, is obtained.

$$M1' = M1 - 1/10(L2) = L1 + \beta(L3)$$

The pixel value Y1 of the first image P1 includes the noise component $1/10(L2)$, so the noise component $1/10(L2)$ is removed from the pixel value Y1. Thereby, a corrected pixel value Y1', having only the component corresponding to the fluorescence L3, is obtained.

$$Y1' = Y1 - 1/10(L2) = L3$$

Note that, for the L2, a value obtained from the expressions (X1), (X4), and (X7) is used as shown below.

$$L2 = 100/99\{(C2 - 1/10(C1)) - 72/91(Y1)\}$$

The corrected pixel values C2', M1', and Y1' are converted into B, G, and R values of the additive color system. A well-known method is used for converting the CMY of the subtractive color system into the R, G, and B values of the additive color system. The converted B value corresponds to the corrected pixel value b2' of the above embodiment. The converted G value corresponds to the corrected pixel value g1' of the above embodiment. The converted R value corresponds to the pixel value r1 of the above embodiment. The oxygen saturation level is calculated based on the R, G, and B values in a manner similar to the above embodiment. Note that it is preferable to check whether the relation between the emission intensity and the converted pixel values is appropriate.

In the above embodiment, the pixel values C2, M1, and Y1 are used for calculating the oxygen saturation level. Alternatively, the oxygen saturation level may be calculated using other pixel values, for example, C1, M2, and Y2. In this case, the pixel value Y2 does not have a noise component. Accordingly, a noise component is removed from the pixel values C1 and M2 to obtain the corrected pixel values C1' and M2'. The corrected pixel values C1' and M2' and the pixel value Y2 are converted into the R, G, and B values. The oxygen saturation level is calculated based on the converted R, G, and B values. Note that the noise component in the pixel value C1 is $1/10(L2)$. The noise component in the pixel value M2 is $1/10(L1)$ and $\beta \times 9/10(L3)$.

In the above embodiments, the two semiconductor light sources are used by way of example. At least one semiconductor light source is used. In this case, in the vascular observation mode, light source(s) other than the semiconductor light source is turned on and off repeatedly, while the semiconductor light source is switched alternately between the full and reduced light states. The light may not be reduced for the unit of the accumulation and readout periods of the CCD 33. For example, the light may be in full or reduced light state in two consecutive frames. Furthermore, the light may be reduced at irregular intervals. For example, one of the light is reduced in one frame and then the other light may be reduced in the consecutive two frames. In a word, the semiconductor light source is kept turned on without being turned off. When the noise component corresponding to the reduced illumination light is negligible, the reduction of the noise component may be omitted.

Two or more types of narrowband light, for example, four types of narrowband light with the center wavelengths of, for example, 405 nm, 450 nm, 550 nm, and 780 nm may be applied to the internal body portion to obtain the vascular images of the mucosal superficial, middle, and deep layers. A fluorescent substance may be ejected into living tissue and excitation light may be applied to the living tissue to observe fluorescence from the living tissue, or intrinsic fluorescence of the living tissue may be observed. Alternatively, the wavelength converter 64 may be disposed in front of the first semiconductor laser 55. The wavelength converter 64 is inserted into a light path of the first semiconductor laser 55 in the normal observation mode.

In the above embodiments, the electronic endoscope is described by way of example. Instead, an endoscope of a different type, for example, an ultrasonic endoscope incorporating an imaging device and an ultrasonic transducer at its tip may be used.

In the present invention, an image of the oxygen saturation level is produced. Alternatively or in addition, an image of information on, for example, oxyhemoglobin index or deoxyhemoglobin index may be produced. The oxyhemoglobin index is obtained from "blood volume (sum of oxyhemoglobin and deoxyhemoglobin)×oxygen saturation level (%)". The deoxyhemoglobin index is obtained from "blood volume×(100-oxygen saturation level) (%)".

Various changes and modifications are possible in the present invention and may be understood to be within the present invention.

What is claimed is:

1. An electronic endoscope system comprising:
at least first and second light source systems configured to illuminate an internal body portion including a blood vessel from an insert section to be inserted into a body, the first light source system generating first illumination light including first narrowband light, the second light source system generating second illumination light including second narrowband light, the first light source system having a first semiconductor light source, the second light source system having a second semiconductor light source, wherein a lens through which both the first and second light are transmitted is physically situated in a same organ of interest, and wherein each of the first illumination light and the second illumination light has a different emission spectra;
a color imaging device configured to image the internal body portion illuminated with the first or second illumination light, the color imaging device having pixels of two or more colors, electric charge accumulated in each pixel being read out periodically as a pixel value, wherein the color imaging device outputs a first image captured under illumination of the first illumination light, and a second image captured under illumination of the second illumination light;
a controller configured to control the first and second light source systems such that the first and second illumination light is applied alternately to the internal body portion in a vascular observation mode, the controller putting the second semiconductor light source of the second light source system into the reduced light state without turning off the second semiconductor light source during the application of the first illumination light and putting the first semiconductor light source of the first light source system into a reduced light state without turning off the first semiconductor light source during the application of the second illumination light;
a processor configured to:
calculate and remove a first noise component and a second noise component from the pixel value, used for imaging of vascular information of the internal body portion, with a use of correlation operation of the pixel values of the two or more colors, to calculate a corrected pixel value, the first noise component being a signal component obtained under illumination of the first semiconductor light source in the reduced light state, and the second noise component being a signal component obtained under illumination of the second semiconductor light source in the reduced light state; and
produce a vascular information image based on the corrected pixel value, wherein the vascular information image is produced based on two frames of the first and second images; and
a display controller configured to cause the vascular information image to be displayed.

2. The electronic endoscope system according to claim 1, wherein one of the first and second light source systems is alternately put into the reduced light state for a charge accumulation period of the pixel.

3. The electronic endoscope system according to claim 2, wherein illumination of a first emission pattern and illumination of a second emission pattern is applied alternately in the vascular observation mode, and the first emission pattern is a mixture of the second illumination light in the reduced light state and the first illumination light, and the second emission pattern is a mixture of the first illumination light in the reduced light state and the second illumination light.

4. The electronic endoscope system according to claim 3, wherein the first light source system has the first semiconductor laser which is configured to generate the first narrowband light and a wavelength converter which is configured to generate fluorescence in a wavelength range from green to red upon excitation with the first and second narrowband light,
and the second light source system has the second semiconductor laser which is configured to generate the second narrowband light and the wavelength converter shared with the first light source system.

5. The electronic endoscope system according to claim 4, wherein, the first narrowband light has an emission peak in a blue wavelength range;
the second narrowband light has an emission peak in a wavelength range from blue and green;
the fluorescence is broadband light in a wavelength range from green to red;
the first illumination light is a mixture of the fluorescence from the wavelength converter excited by the first narrowband light, and the first narrowband light passed through the wavelength converter; and
the second illumination light is a mixture of the fluorescence from the wavelength converter excited by the second narrowband light, and the second narrowband light passed through the wavelength converter.

6. The electronic endoscope system according to claim 5, wherein the two or more colors are red, green, and blue, and
red and green pixel values obtained under the illumination of the first emission pattern and a blue pixel value obtained under the illumination of the second emission pattern are used for producing the vascular information image.

7. The electronic endoscope system according to claim 6, wherein the processor removes the second noise component from the green pixel value obtained under the illumination of the first emission pattern, and removes the first noise component from the blue pixel value obtained under the illumination of the second emission pattern.

8. The electronic endoscope system according to claim 5, wherein the two or more colors are cyan, magenta, and yellow, and
magenta and yellow pixel values obtained under the illumination of the first emission pattern and a cyan pixel value obtained under the illumination of the second emission pattern are used for producing the vascular information image.

9. The electronic endoscope system according to claim 8, wherein the processor removes the noise component, caused by the second illumination light in the reduced light state, from the magenta and yellow pixel values obtained under the illumination of the first emission pattern, and removes a noise component, caused by the first illumination light in the reduced state, from the cyan pixel value obtained under the illumination of the second emission pattern.

10. The electronic endoscope system according to claim 5, wherein the vascular information is an oxygen saturation level of hemoglobin in blood in the blood vessel, and the blood vessels in the vascular information image are color-coded in accordance with the oxygen saturation level.

11. The electronic endoscope system according to claim 10, further includes a normal observation mode, and in the normal observation mode the internal body portion is illuminated with the first illumination light.

12. A method for controlling an electronic endoscope system having at least first and second light source systems for illuminating an internal body portion including a blood vessel from an insert section to be inserted into a body, the first light source system generating first illumination light including first narrowband light, the second light source system generating second illumination light including second narrowband light, the first light source system having a first semiconductor light source, the second light source system having a second semiconductor light source, the method comprising the steps of:

applying first and second illumination light alternately to the internal body portion, both the first and second illumination light being transmitted through a lens physically situated in a same organ of interest, each of the first illumination light and the second illumination light has a different emission spectra, the second semiconductor light source being kept in a reduced light state without being turned off during the application of the first illumination light, the first semiconductor light source of the first light source system being kept in a reduced light state without being turned off during the application of the second illumination light;

imaging the internal body portion with a color imaging device, the color imaging device having pixels of two or more colors, electric charge accumulated in each pixel being read out periodically as a pixel value, wherein the color imaging device outputs a first image captured under illumination of the first illumination light, and a second image captured under illumination of the second illumination light;

calculating and removing first and second noise components from the pixel value, used for imaging of vascular information of the internal body portion, with a use of correlation operation of the pixel values of the two or more colors, to calculate a corrected pixel value, the first and second noise components being signal components respectively obtained under illumination of the first semiconductor light source and the second semiconductor light source in the reduced light state producing a vascular information image based on the corrected pixel value, wherein the vascular information image is produced based on two frames of the first and second images; and displaying the vascular information image on a display section.

* * * * *